US00PP36415P2

(12) United States Plant Patent
Kenworthy

(10) Patent No.: US PP36,415 P2
(45) Date of Patent: Jan. 28, 2025

(54) ZOYSIAGRASS PLANT NAMED 'FAES1319'

(50) Latin Name: *Zoysia japonica Steud.*
Varietal Denomination: FAES1319

(71) Applicant: Florida Foundation Seed Producers, Inc., Marianna, FL (US)

(72) Inventor: Kevin E. Kenworthy, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/410,652

(22) Filed: Jan. 11, 2024

(51) Int. Cl.
*A01H 5/12* (2018.01)
*A01H 6/46* (2018.01)

(52) U.S. Cl.
USPC ..... Plt./390

(58) Field of Classification Search
USPC ..... Plt./390
See application file for complete search history.

(56) References Cited

U.S. PATENT DOCUMENTS

PP11,466 P 8/2000 Ito et al.
PP13,166 P2 11/2002 Doguet
PP27,051 P3 8/2016 Chapman

OTHER PUBLICATIONS www.https://ntep.org "National Turfgrass Evaluation Program" (Retrieved from the Internet on May 19, 2024)(5 pages only).*

* cited by examiner

*Primary Examiner* — Susan McCormick Ewoldt
(74) *Attorney, Agent, or Firm* — Dentons US LLP

(57) ABSTRACT

'FAES1319' is a new and distinct zoysiagrass (*Zoysia japonica* Steud.) variety distinguished at least by its medium leaf texture, high turfgrass quality, good shade tolerance, good winter color retention, good spring green up, and low incidence of large patch disease caused by *Rhizoctonia solani* anastomosis group 2-2 LP. It has exhibited broad adaptation to contrasting environments from the Southern U.S. and north into the Transition Zone.

3 Drawing Sheets

ACKNOWLEDGEMENT OF FEDERAL RESEARCH SUPPORT

This invention was made with government support under 2015-51181-24291 awarded by the National Institute of Food and Agriculture, United States Department of Agriculture (U.S.D.A.). The government has certain rights in the invention.

Latin name of the genus and species of the plant claimed: *Zoysia japonica* Steud.

Variety denomination: 'FAES1319'.

BACKGROUND OF THE INVENTION

The present invention relates to a new and distinct asexually reproduced variety of zoysiagrass (*Zoysia japonica* Steud.) designated 'FAES1319'. The parents of the zoysiagrass 'FAES1319' are unknown. 'FAES1319' was selected as an individual plant in 2008 from a cultivated area located in Parkland, FL. This cultivated area was planted with various zoysiagrasses, mostly *Zoysia matrella* plants interspersed with *Zoysia japonica* plants. 'FAES1319' was first asexually propagated in Citra, FL in 2008 through vegetative cuttings of stolons that were planted and rooted in potting media. Asexually reproduced plants of 'FAES1319' have remained stable and true to type through at least six successive cycles of this vegetative propagation. 'FAES1319' has been determined to be tetraploid (2n=4x=40).

SUMMARY OF THE INVENTION

'FAES1319' is a perennial zoysiagrass that spreads by stolons and rhizomes, and was identified based on its superior attributes from a collection of zoysiagrass plants that were evaluated for turfgrass quality traits in Citra, FL under cultivated conditions. 'FAES1319' can be unambiguously distinguished by its medium leaf texture, high turfgrass quality, good shade tolerance, good winter color retention, good spring green up, and low incidence of large patch disease caused by *Rhizoctonia solani* anastomosis group 2-2 LP. 'FAES1319' may also be distinguished by the broad growing range in which it exhibits high to good turfgrass quality. 'FAES1319' may be used as a turfgrass that is suitable for home lawns and commercial turf applications. The observed cool season turfgrass quality, color retention, and shade tolerance of 'FAES1319' indicates that it is well-suited to the southern and central areas of the U.S. zoysiagrass adaptation zone, and it should be equally well-suited to other subtropical and tropical areas worldwide where zoysiagrass is cultivated.

BRIEF DESCRIPTION OF THE DRAWINGS

This new zoysiagrass plant is illustrated by the accompanying photographs of plants grown in a Gainesville, FL greenhouse, as provided in FIG. 1 and FIG. 2. These photographs show the plant's typical form, foliage, and inflorescence, and the colors shown are as true as can be reasonably obtained by conventional photographic procedures.

DETAILED BOTANICAL DESCRIPTION

Figure 1:
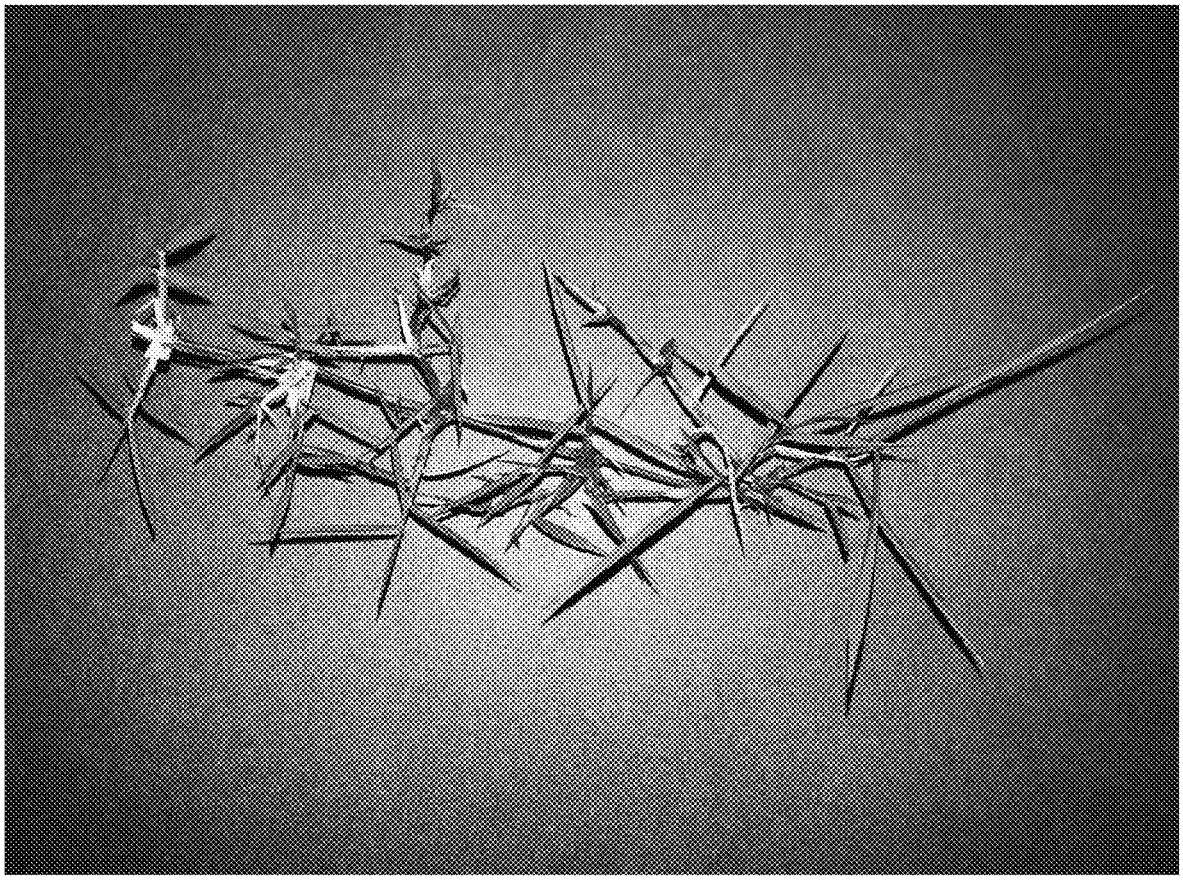
FIG. 1—Shows a stolon of a 3 month old 'FAES1319' plant.
Figure 2:
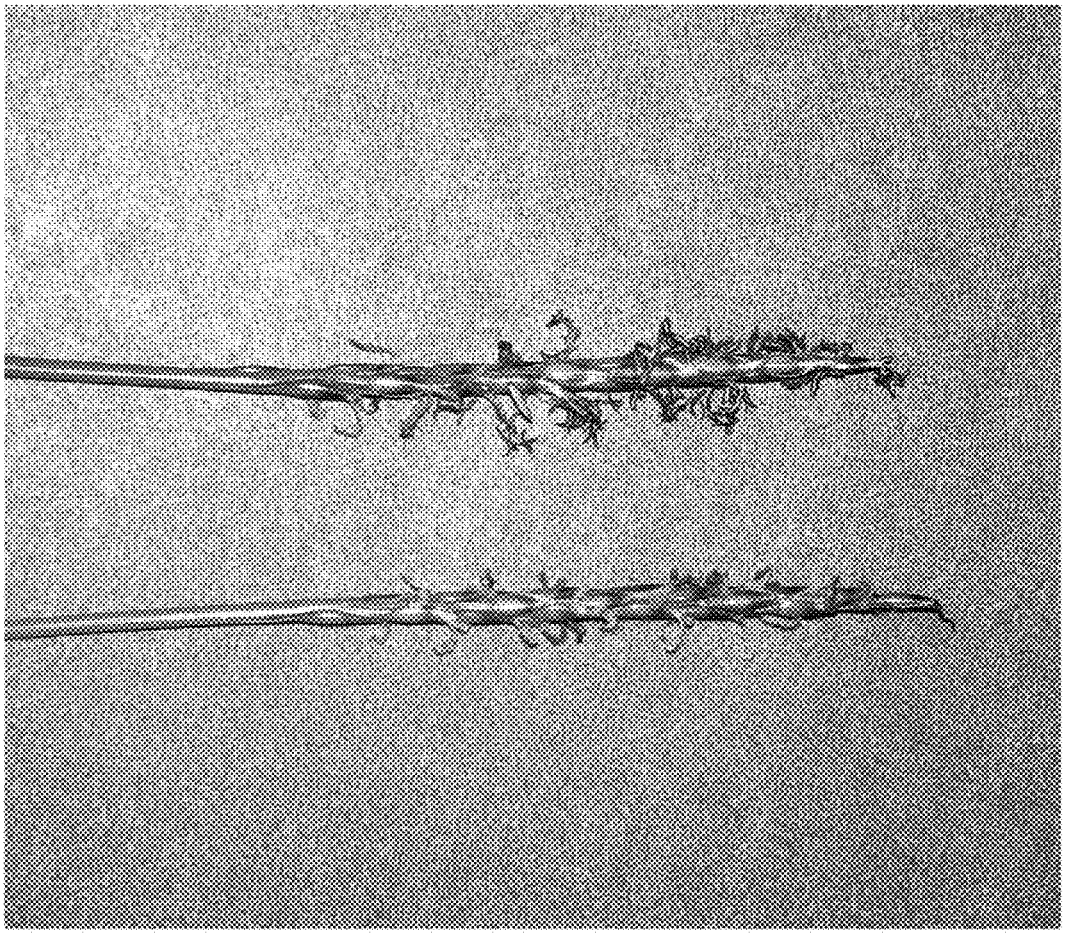
FIG. 2—Shows an inflorescence, including anthers and stigmas, of a 3 month old 'FAES1319' plant.

The following detailed description sets forth distinctive characteristics of 'FAES1319', as characterized in greenhouse and field conditions. The data that define these characteristics were collected from clonally propagated plants. 'FAES1319' has not been observed under all possible environmental conditions, and the measurements given may vary when grown in different environments. Certain characteristics may also vary with plant age. The color descriptions provided herein are based on The Royal Horticultural Society (R.H.S.) Colour Chart by The Royal Horticultural Society, London, Sixth Revised Edition. If any R.H.S. color designations below differ from the accompanying photographs, the R.H.S. color designations are accurate.

MORPHOLOGICAL COMPARISON OF 'FAES1319' TO COMMERCIAL AND EXPERIMENTAL VARIETIES

The morphological characteristics of 'FAES1319' and commercial zoysiagrass varieties 'SS-500' (U.S. Plant Pat. No. 11,466) and 'BK-9' (U.S. Plant Pat. No. 27,051), and experimental varieties 'FAES1312' (*Zoysia japonica* (L) Merr.) and 'FAES1313' (*Zoysia japonica* Steud.) were evaluated in 2015 and 2016 from greenhouse potted plants that were approximately 6 months in age; arrangement was a randomized complete block design with three replications. Three samples were measured for each trait from each pot and averaged to represent the replication. Leaf length (cm) and width (mm) were measured on the second fully expanded leaf below the growing meristem of a stolon. Average internode length and stolon diameter were determined through measuring the third internode back from the growing point of three different stolons growing over the edge of the pots. The greenhouse was located near Gainesville, FL., with a daily temperature range of 15° C., and daytime high of 33° C. The plants were grown under natural day length without supplemental lighting. The plants were fertilized with the equivalent of 0.45 kg N per month, using a soluble fertilizer of 20-20-20 ($N—P_2O_5—K_2O$) in four equal soluble applications per month. Data were averaged across dates and provided in Table 1.

'FAES1319' exhibited a leaf width that was significantly less than that of 'SS-500' but significantly greater than that of 'BK-9'. 'FAES1319' also exhibited a leaf blade length that was longer than that of 'BK-9' but similar to that of 'SS-500'. The average observed internode length and stolon diameter of 'FAES1319' were both similar to those of both 'BK-9' and 'SS-500'.

The following are additional unique and distinguishing characteristics exhibited by 'FAES1319' when grown under the above greenhouse conditions:

PLANT

Growth habit: A perennial plant that spreads by stolons and rhizomes, and produces a dense, medium textured turfgrass.

Leaves:
- *Leaf blade color adaxial leaf surface.*—146A Moderate Olive Green to moderate yellowish green.
- *Leaf blade color abaxial leaf surface.*—146A Moderate Olive Green.
- *Attachment.*—Sheathing.
- *Shape.*—Linear.
- *Apex shape.*—Acute.
- *Aspect.*—Semierect.
- *Texture.*—Smooth with occasional fine hairs (upper surface); smooth (lower surface).
- *Margins.*—Entire.
- *Venation.*—Parallel.
- *Leaf collar.*—Continuous and narrow.
- *Ligule.*—Hairy.
- *Auricle.*—None.

Stolon color (in absence of light): 144A strong yellow green.

INFLORESCENCE

Time of flowering: March-July in Gainesville, FL. Produces primarily terminal spike-like racemes, with spikelets on short appressed pedicels. The spikelets generally occur singularly appressed against the slender rachis.

Culm stalk color: 138B Moderate Yellow Green.

Average rachis length: 21 mm.

Floret size: 2.3-2.4 mm.

Floret shape: Elliptic.

Floret color:
- *1st and 2nd glume color.*—79B Dark Purple.
- *Palea color.*—157D Greenish White.
- *Lemma color.*—157D Greenish White.
- *Stigma shape.*—Feathery.
- *Stigma color.*—155B yellowish white.
- *Anther (fresh) color.*—83C strong purple.

Ovary:
- *Size.*—0.5-0.7 mm.
- *Color.*—*NN*155B White

Caryopses:
- *Size.*—0.8-1.0 mm.
- *Shape.*—Oval.
- *Color.*—161C Pale Yellow.

TURFGRASS QUALITY, FALL COLOR, DENSITY AND SHADE TOLERANCE COMPARISON OF 'FAES1319' TO COMMERCIAL AND EXPERIMENTAL VARIETIES

'FAES1319' was entered into the 2013 National Turfgrass Evaluation Program (NTEP) trials to evaluate its long-term performance under multiple environments. Persistence through time is weighted heavily when considering the merit of a turfgrass. These trials were conducted over 17 locations throughout the U.S. and utilized 'SS-500', 'Meyer' (unpatented), and 'Zeon' (U.S. Plant Pat. No. 13,166) as the check varieties. Additionally, data can be selected for specific assessment of a genotype's performance in a location, region, or season to identify areas of adaptation. All trials were arranged as randomize complete block designs with three replications and planted with 24 5.0×5.0 cm plugs in 2013. Turfgrass quality was rated on a "1" to "9" scale in which "9" indicates "best," "6" indicates "minimally accepted," and "1" indicates "poorest"; turfgrass color was rated on a "1" to "9" scale in which "9" indicates the darkest green, "1" is brown; and turfgrass density was rated on a "1" to "9" scale in which "9" indicates "best," "6" indicates "minimally accepted," and "1" indicates "poorest." Plots were rated following establishment from 2014-2017.

Trial means from 2014-2017 trials are presented in Table 2 and Table 3. Fall color from November in Dallas, TX and Citra, FL, density in Citra FL, and turfgrass quality from Citra, FL and Jay, FL are found in Table 2. Table 3 contains the average turfgrass quality from 14 locations (Locations averaged were Alabama, Arkansas, Arizona, Jay, FL, Citra, FL, Georgia, Indiana, Kansas, Maryland, Missouri, North Carolina, Tennessee, Dallas, TX, and College Station, TX) and Manhattan, KS to illustrate the broad adaptation of 'FAES1319' and its cold tolerance, and shade tolerance in Riverside, CA.

The fall color retention of 'FAES1319' was better than that of 'Meyer' in both Dallas, TX and Citra, FL (Table 2). 'FAES1319' also had better fall color than 'SS-500' in Citra, FL. The fall color of 'Zeon' was similar to 'FAES1319' at both locations. The average density of 'FAES1319' was higher than the average density ratings of 'Meyer', 'SS-500', and 'Zeon' in Citra, FL. The average turfgrass quality of 'FAES1319' was higher than the quality of 'Meyer' and 'SS-500' at Citra, FL and Jay, FL. Additionally, in Citra, FL the quality of 'FAES1319' was better than the quality observed for 'SS-500' and 'Zeon'.

Averaging across the 14 locations from 2014-2017 resulted in 'FAES1319' having higher turfgrass quality than 'Meyer', 'SS-500', and 'Zeon' (Table 3). In Manhattan, KS, the turfgrass quality of 'FAES1319' was not different from any check cultivar. 'Meyer' zoysiagrass is considered the industry standard for cold tolerance. Considering the average performance across locations and its performance in Manhattan, KS, 'FAES1319' is broadly adapted and has good cold tolerance. 'FAES1319' is also adapted to shade. 'Zeon' exhibits excellent shade tolerance. The quality of 'FAES1319' under shade in Riverside, CA was equivalent to 'Zeon' and better than the quality of 'Meyer' and 'SS-500'.

LARGE PATCH DISEASE RESPONSE OF 'FAES1319'

Figure 3:
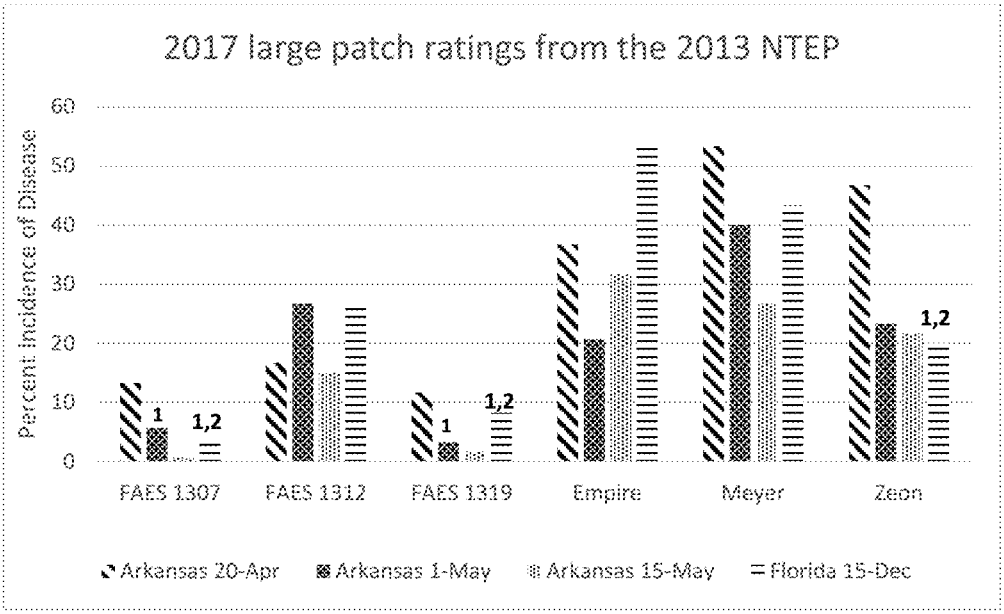
FIG. 3—Shows percent incidence of large patch disease (*Rhizoctonia solani*) in 2017 of 'FAES1319' in comparison to commercial and experimental zoysiagrass genotypes from the 2013 National Turfgrass Evaluation Program zoysiagrass trial. Numbers over a column indicate that the column entry was significantly different from the entry number as determined by the following: 1=entry better than 'SS-500', 2=entry better than 'Zeon', and 3=entry better than 'Meyer'.

Large patch, caused by *Rhizoctonia solani* anastomosis group 2-2 LP is the most important disease of zoysiagrass. Large patch response data was collected in 2017 as part of the 2013 Zoysiagrass NTEP trial (described above) from Arkansas and Florida. The observed percent incidence of disease of large patch at the Florida location was less severe for 'FAES1319' than for the 'Meyer' and 'SS-500'; whereas, in Arkansas, disease was less for 'FAES1319' on May 1, 2017 compared to 'Meyer' (FIG. 3).

TABLE 1

Morphological comparison of 'FAES1319' and commercial and experimental zoysiagrasses.

| Variety | Leaf length | Leaf width | Internode length | Stolon diameter |
|---|---|---|---|---|
| 'FAES1319' | 9.05 | 3.33 | 18.78 | 1.54 |
| 'SS-500' | 9.11 | 4.22 | 14.44 | 1.74 |
| 'BK-9' | 5.78 | 2.00 | 13.78 | 1.32 |
| 'FAES1312' | 7.95 | 3.78 | 9.22 | 1.60 |
| 'FAES1313' | 8.00 | 3.00 | 10.43 | 1.31 |
| LSD (p = 0.05)* | 1.43 | 0.38 | 7.36 | 0.25 |

*Values within a column that differ by more than the LSD value are significantly different.

TABLE 2

Average (2014-2017) fall color, density and turfgrass quality of 'FAES1319' and commercial and experimental zoysiagrasses.

| | Average values from 2014-2017 | | | | |
|---|---|---|---|---|---|
| | Fall Color | | Density | Quality | |
| Variety | Dallas, TX | Citra, FL | Citra, FL | Citra, FL | Jay, FL |
| 'FAES1319' | 5.2 | 5.2 | 7.7 | 6.1 | 6.7 |
| 'Meyer' | 3.3 | 3.7 | 4.8 | 3.2 | 6.0 |
| 'SS-500' | 4.0 | 4.0 | 6.5 | 4.8 | 6.2 |
| 'Zeon' | 4.0 | 4.5 | 6.5 | 5.1 | 6.1 |
| 'FAES1312' | 4.3 | 4.7 | 7.1 | 6.0 | 6.5 |
| 'FAES1313' | 4.8 | 5.7 | 7.1 | 6.2 | 6.3 |
| LSD (p = 0.05)* | 1.4 | 0.8 | 1.1 | 0.7 | 0.6 |

*Values within a column that differ by more than the LSD value are significantly different.

TABLE 3

Average (2014-2017) turfgrass quality across 14 locations and at Manhattan, KS and shade tolerance in Riverside, CA of 'FAES1319' and commercial and experimental zoysiagrasses.

| | Average values from 2014-2017 | | |
|---|---|---|---|
| Variety | Turfgrass Quality 14 locations‡ | Turfgrass Quality Manhattan, KS | Turfgrass Quality Shade Riverside, CA |
| 'FAES1319' | 6.3 | 6.4 | 5.6 |
| 'Meyer' | 5.4 | 6.2 | 4.5 |
| 'SS-500' | 5.7 | 5.6 | 4.9 |
| 'Zeon' | 5.9 | 6.8 | 5.5 |
| 'FAES1312' | 6.2 | 6.2 | 5.4 |
| 'FAES1313' | 6.1 | 5.3 | 4.7 |
| LSD (p = 0.05)* | 0.3 | 1.1 | 0.4 |

*Values within a column that differ by more than the LSD value are significantly different.
‡Locations averaged were Alabama, Arkansas, Arizona, Jay, FL, Citra, FL, Georgia, Indiana, Kansas, Maryland, Missouri, North Carolina, Tennessee, Dallas, TX, and College Station, TX.

What is claimed is:

1. A new and distinct variety of zoysiagrass plant named 'FAES1319', as illustrated and described herein.

* * * * *